(12) United States Patent
Gupta et al.

(10) Patent No.: US 10,029,106 B2
(45) Date of Patent: Jul. 24, 2018

(54) REMOTE ACCESS AND POST PROGRAM TELEMONITORING

(71) Applicant: Boston Scientific Neuromodulation Corporation, Valencia, CA (US)

(72) Inventors: Swati Gupta, Douglas (AU); Jessica C. Martin, Ascot Vale (AU); Dennis Zottola, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 34 days.

(21) Appl. No.: 15/222,273

(22) Filed: Jul. 28, 2016

(65) Prior Publication Data
US 2017/0050035 A1   Feb. 23, 2017

Related U.S. Application Data

(60) Provisional application No. 62/206,184, filed on Aug. 17, 2015.

(51) Int. Cl.
*A61N 1/36* (2006.01)
*A61N 1/372* (2006.01)

(52) U.S. Cl.
CPC ..... *A61N 1/37264* (2013.01); *A61N 1/36021* (2013.01); *A61N 1/36071* (2013.01); *A61N 1/37211* (2013.01); *A61N 1/37247* (2013.01)

(58) Field of Classification Search
None
See application file for complete search history.

(56) References Cited

U.S. PATENT DOCUMENTS 5,544,649 A * 8/1996 David ................. A61B 5/6887
128/904
7,848,819 B2 * 12/2010 Goetz ................. G06F 19/3481
607/31

(Continued)

FOREIGN PATENT DOCUMENTS

WO   WO-2017030763 A1   2/2017

OTHER PUBLICATIONS

"Theapy Options for Managing Your Chronic Pain", Boston Scientific Brochure, "Precision Spectra™ Spinal Cord Stimulator System", Sep. 2013, 20 pgs.

(Continued)

*Primary Examiner* — Kennedy Schaetzle
(74) *Attorney, Agent, or Firm* — Schwegman Lundberg & Woessner, P.A.

(57) ABSTRACT

A system may include a therapy controller including a telemetry circuit configured to communicate with an implantable or wearable medical device and a processor configured to execute instructions relating to programming the implantable medical device, and a communication circuit operatively coupled to the therapy controller and configured to transfer information between the therapy controller and a remote device. The therapy controller is configured to receive at least one input relating to operation of the implantable medical device, convert the input into proposed programming instructions, apply device programming rules to verify the safety of the proposed programming instructions, and deliver the programming instructions to the implantable or wearable medical device. In an example, the therapy controller is also configured to deliver information about the programming and data from the IPG, such as various data reporting on the IPG status to a remote device using the communication circuit.

20 Claims, 7 Drawing Sheets

(56) References Cited

U.S. PATENT DOCUMENTS

| | | | |
|---|---|---|---|
| 7,885,712 | B2 | 2/2011 | Goetz et al. |
| 8,738,155 | B2 | 5/2014 | Zhu et al. |
| 2003/0120324 | A1 | 6/2003 | Osborn et al. |
| 2007/0203543 | A1* | 8/2007 | Stone ............... A61N 1/37247 607/59 |
| 2007/0255346 | A1 | 11/2007 | Rondoni et al. |
| 2008/0221644 | A1 | 9/2008 | Vallapureddy et al. |
| 2009/0058635 | A1 | 3/2009 | LaLonde et al. |
| 2009/0264955 | A1 | 10/2009 | Giftakis et al. |
| 2010/0030303 | A1* | 2/2010 | Haubrich ............... A61N 1/08 607/60 |
| 2012/0271380 | A1* | 10/2012 | Roberts ............. A61N 1/37252 607/60 |
| 2012/0296398 | A1 | 11/2012 | Aghassian |
| 2013/0154851 | A1 | 6/2013 | Gaskill et al. |
| 2014/0364920 | A1 | 12/2014 | Doan et al. |
| 2015/0073504 | A1 | 3/2015 | Kothandaraman et al. |
| 2015/0238762 | A1* | 8/2015 | Pal ..................... A61N 1/0476 607/45 |
| 2016/0038733 | A1* | 2/2016 | Robinson ............ A61N 1/0534 607/116 |
| 2016/0246935 | A1* | 8/2016 | Cerny ................. G06F 19/3406 |

OTHER PUBLICATIONS

Zhang, et al., "A Remote and Wireless Deep Brain Stimulation", Neuromodulation: Technology at the Neural Interface, 19:437-439, 2016 International Neuromodulation Society.

"International Application Serial No. PCT/US2016/044460, International Search Report dated Oct. 11, 2016", 4 pgs.

"International Application Serial No. PCT/US2016/044460, Written Opinion dated Oct. 11, 2016", 5 pgs.

* cited by examiner

REMOTE ACCESS AND POST PROGRAM TELEMONITORING

CLAIM OF PRIORITY

This application claims the benefit of priority under 35 U.S.C. § 119(e) of U.S. Provisional Patent Application Ser. No. 62/206,184, filed on Aug. 17, 2015, which is herein incorporated by reference in its entirety.

TECHNICAL FIELD

This document relates generally to medical devices, and more particularly, to systems, devices and methods for remotely configuring medical devices such as neurostimulation devices.

BACKGROUND

Many medical devices have programmable settings that allow for configuration of operational settings that control therapy or diagnostic functions.

Programmable neural modulation is used in a variety of forms, such as for pain management, and has been proposed as a therapy for a number of conditions. In some instances, "neural modulation" and "neural stimulation" may be used interchangeably to describe excitatory stimulation that causes action potentials as well as inhibitory and other effects.

Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Some neural targets may be complex structures with different types of nerve fibers. An example of such a complex structure is the neuronal elements in and around the spinal cord targeted by SCS. This complexity may contribute to difficulties in placing modulation electrodes and difficulties in programming the modulation field(s) in different patients, as the optimal placement of the modulation electrodes and the optimal modulation field to treat a specific pain area can vary among patients.

SCS is often delivered using an implantable system. The implantable system is typically programmed in a health care facility by an individual (e.g. a doctor) who is interacting with a patient.

SUMMARY

An example (e.g. "Example 1") of subject matter (e.g. a system) may include a therapy controller including a telemetry circuit configured to communicate with an implantable or wearable medical device and a processor configured to execute instructions relating to programming the implantable medical device. The therapy controller may include a communication circuit operatively coupled to the therapy controller and configured to transfer information between the therapy controller and a remote device. The therapy controller may be configured to receive at least one input relating to operation of the implantable medical device, convert the input into proposed programming instructions, apply device programming rules to verify the safety of the proposed programming instructions, and deliver the programming instructions to the implantable or wearable medical device when the programming instructions comply with the rules.

In Example 2, the subject matter of Example 1 may optionally be configured such that the therapy controller is configured to deliver information about the programming to a remote device using the communication circuit.

In Example 3, the subject matter of Example 1 may optionally include patient feedback device configured to receive feedback information from a patient. The controller may be configured to deliver the feedback information from the patient to the remote device using the communication circuit.

In Example 4, the subject matter of Example 1 may optionally include a camera and the feedback information includes at least one image of a facial expression or body position or movement of a patient.

In Example 5, the subject matter of any one or any combination of Examples 3 or 4 may optionally include a patient feedback device that is configured to capture one or more of a verbal report, a visual indication, and a keyboard input.

In Example 6, the subject matter of any one or any combination of Examples 3-5 may optionally be configured such that the patient feedback device includes a sensor configured to measure one or more physiological responses.

In Example 7, the subject matter of any one or any combination of Examples 3-6 may optionally include a display configured to present to the patient at least one image of a person who is remotely providing the at least one input relating to operation of the implantable medical device In Example 8, the subject matter of any one or any combination of Examples 2-7 may optionally include an implantable or wearable medical device or external stimulator configured to deliver stimulation therapy to a patient.

In Example 9, the subject matter of any one or any combination of Examples 1-8 may optionally be configured such that the therapy controller is configured to execute a verification step that confirms the proposed programming instructions are consistent with the input received into the remote device.

In Example 10, the subject matter of any one or any combination of Examples 1-9 may optionally be configured such that the therapy controller is configured to convert at least one input received by the controller into proposed programming instructions in the same manner and subject to the set of device programming rules executed by the therapy controller, regardless of the origin of the input.

In Example 11, the subject matter of any one or any combination of Examples 1-10 may optionally be configured such that the therapy controller includes a user interface circuit configured to receive an input relating to operation of the implantable medical device, and the controller is configured to convert at least one input into programming instructions and apply device programming rules in the same manner regardless of whether the input originated from the therapy controller user interface or the remote device.

In Example 12, the subject matter of Example 11 may optionally be configured such that therapy controller includes a circuit configured to execute user-interface automation instructions to convert the inputs relating to operation of the implantable or wearable medical device into the proposed programming instructions.

In Example 13, the subject matter of any one or any combination of Examples 1-12 may optionally be configured such that the communication circuit is configured to monitor the quality a network connection to a remote device and send a signal to the therapy controller to refrain from implementing programming changes when the network connection does not meet specified criteria.

In Example 14, the subject matter of Example 13 may optionally be configured such that the therapy controller is configured to ramp up or down the strength of a stimulation therapy, and stop the ramp up or down in response to receipt of a signal from the communication device that the network connection does not meet specified criteria.

In Example 15, the system of any one or any combination of Examples 1-14 may optionally be configured such that the therapy controller is configured to receive an instruction to download a previously-verified program from a remote device, and install the program on the therapy controller.

An Example ("Example 16") of subject matter (e.g. a system) may include a therapy controller including a telemetry circuit configured to communicate with an implantable or wearable medical device and a processor configured to execute instructions relating to programming the implantable medical device, a communication circuit operatively coupled to the therapy controller and configured to transfer information between the therapy controller and a remote device. The therapy controller may be configured to receive at least one input relating to operation of the implantable medical device, convert the input into proposed programming instructions, apply device programming rules to verify the safety of the proposed programming instructions, deliver the programming instructions to the implantable or wearable medical device when the programming instructions comply with the rules, and deliver information about the programming to a remote device using the communication circuit.

In Example 17, the subject matter of Example 16 may optionally include a patient feedback device configured to receive feedback information from a patient, and the therapy controller may optionally be configured to deliver the feedback information from the patient to the remote device using the communication circuit.

In Example 18, the subject matter of Example 17 may optionally be configured such that the patient feedback device includes a camera and the feedback information includes at least one image of a facial expression or body position or movement of a patient.

In Example 19, the subject matter of any one or any combination of Examples 17-18 may optionally be configured such that the patient feedback device is configured to capture one or more (or all) of a verbal report, a visual indication, a keyboard input, and sensed physiologic information from the patient.

In Example 20, the subject matter of any one or any combination of Examples 17-19 may optionally be configured such that the patient feedback device includes a display configured to present to the patient at least one image of a person who is remotely providing the at least one input relating to operation of the implantable medical device.

In Example 21, the subject matter of any one or any combination Examples 16-20 may optionally include an implantable or wearable medical device or external stimulator configured to deliver stimulation therapy to a patient.

In Example 22, the subject matter of any one or any combination Examples 16-21 may optionally be configured such that the therapy controller includes a user interface circuit configured to receive the input relating to operation of the implantable medical device, and the controller is configured to convert at least one input into programming instructions and apply device programming rules in the same manner regardless of whether the input originated from the therapy controller or the remote device.

In Example 23, the subject matter of any one or any combination Examples 16-22 may optionally be configured such that the therapy controller includes a circuit configured to execute user-interface automation instructions to convert the inputs relating to operation of the implantable or wearable medical device into the proposed programming instructions.

In Example 24, the subject matter of any one or any combination of Examples 16-23 may optionally be configured such that the therapy controller is configured to ramp up or down the strength of a stimulation therapy, the communication circuit is configured to monitor the quality a network connection to a remote device, and the therapy controller is configured to stop the ramp up or down in response to receipt of a signal from the communication device that the network connection does not meet specified criteria.

In Example 25, the subject matter of any one or any combination of Examples 16-24 may optionally be configured such that the therapy controller is configured to receive an instruction to download a previously-verified program from a remote device, and install the program on the therapy controller.

An Example ("Example 26") of subject matter (e.g. a system) includes a medical device including a patient circuit configured to interact with a the body of a patient and a telemetry circuit configured to communicate with another device, a therapy controller including a telemetry circuit configured to communicate with the medical device, a communication circuit configured to receive inputs from a remote device over a network, a user interface circuit configured to receive inputs relating to operation of the implantable medical device, and a processor configured to execute instructions relating to programming an implantable medical device. The therapy controller may be configured to convert the received inputs into proposed programming instructions, apply device programming rules to verify the safety of the proposed programming instructions, and deliver the programming instructions to an implantable or wearable medical device when the programming instructions comply with the rules. The therapy controller may optionally be configured to convert the inputs into proposed programming instructions and apply device programming rules in the same manner when the inputs are received through the therapy controller user interface and when then inputs are received from the remote device.

In Example 27, the subject matter of Example 26 may optionally include a remote device. The remote device may include a user interface circuit configured to receive the input relating to operation of the medical device, and a communication circuit configured to transfer information to a network for delivery to the therapy controller.

In Example 28, the subject matter of any one or combination of Examples 26-27 may optionally be configured such that the therapy controller is configured to execute user interface automation instructions to convert the received inputs into programming instructions and apply device programming rules.

In Example 29, the subject matter of any one or combination of Examples 26-28 may optionally be configured such that the medical device includes an implantable neurostimulator.

An Example ("Example 30") of subject matter (e.g. a method of controlling the operation of an implantable or wearable medical device) may include receiving through a communication circuit on a therapy controller at least one input from a remote device that relates to operation of the implantable or wearable medical device, converting the at least one input into programming instructions, applying device programming rules to verify the safety of the programming instructions, and delivering the programming instructions to the implantable or wearable medical device when the programming instructions comply with the rules and the implantable or wearable medical device is in range of a telemetry circuit on the therapy controller.

In Example 31, the subject matter of Example 30 may optionally include capturing biofeedback information from the patient to assess whether the operation of the medical device is effective and sending the bio-feedback information to the remote device.

In Example 32, the subject matter of any one or any combination of Examples 30-31 may optionally include capturing at least one image of a facial expression on a patient.

In Example 33, the subject matter of any of examples 30-32 may optionally include receiving direct inputs relating to operation of the implantable or wearable medical device directly through the therapy controller and converting the direct inputs into direct programming instructions. The inputs may be converted into proposed programming instructions in the same manner and subject to the same set of device programming rules, regardless of whether the inputs are received from the remote device or directly through the therapy controller.

In Example 34, the subject matter of any of Examples 30-34 may optionally include monitoring the quality of a network connection to a remote device and refraining from implementing programming changes when the network connection does not meet specified criteria.

In Example 35, the subject matter of any one or any combination of Examples 30-34 may optionally include progressively increasing or decreasing a magnitude of a stimulation therapy, and stopping the progressive increase in magnitude when a network connection with a remote device does not meet specified criteria.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

DETAILED DESCRIPTION

Figure 1:
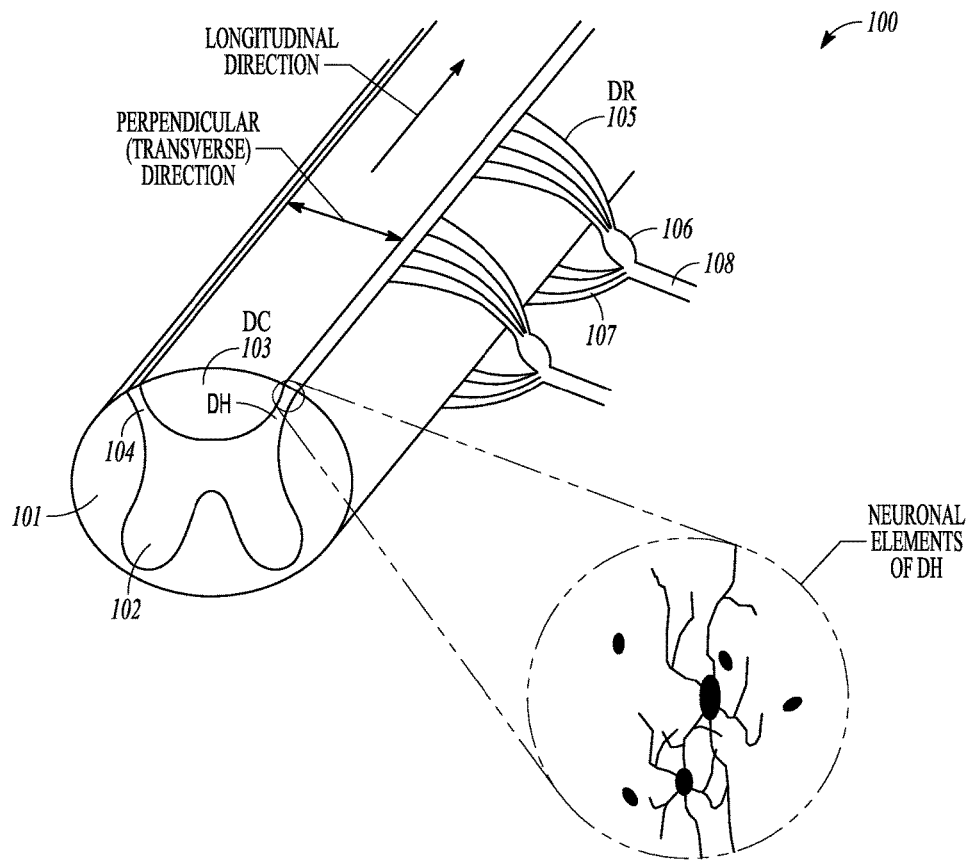
FIG. 1 illustrates a portion of a spinal cord.

The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A remote medical device programming system enables a remote user to safely and securely manipulate programmable features that affect the operation of the device. The features programmed in a medical device are typically set by a health care provider such as a physician. Specific operating parameters may be set by a physician using programmer hardware or software, or the physician may select therapy or diagnostic features which are translated into programming parameters. In an implantable or wearable neurostimulator, for example, electrode combinations and stimulations levels may be selected to deliver appropriate neurostimulation therapy. Device programming is typically performed in a medical facility, but a remote medical device programming system can enable some programming to occur remotely.

Remote access to medical devices can be advantageous for both patients and health care professionals. For example, diagnostics can be run remotely to evaluate the operation of a device or the effectiveness of a therapy, or programming reports can be generated to support trouble-shooting efforts. In some instances, patients whose devices only require minor alterations in device programming can be distinguished from patients who require an in-person consultation. When only a minor alteration is required, the alternation may in some circumstances be performed remotely, i.e. without requiring the patient to physically visit a health care facility where the alteration is prescribed. For example, when a neurostimulator patient who receives stimulation therapy to treat pain, the neurostimulator settings may be adjusted remotely to account for movement of a lead or varying pain levels in a patient. Making adjustments remotely saves the patient the time and expense of traveling to a medical facility, and can be convenient for the physician and efficient for the health care system.

In some instances, a patient can access a limited set of options—e.g. adjusting the intensity of treatment up or down—but the patient cannot access core programming features, such as electrode selection. In an example these features can be accessed remotely by an authorized user to make a minor programming change, such as movement to a different electrode, which may be required when a lead migrates in the body. In some examples, a system can remotely run diagnostics to identify or analyze lead migration using signals detected by electrodes on the leads. When a lead has migrated, the diagnostic information may be used to make programming corrections remotely or in a health care facility.

In some example systems, the system enables interaction between a patient and an individual such as a health care professional who is using a remote device. A neurostimulation system for treating pain, for example, may receive an input from a patient indicating a level of pain, a pain score for a particular day, or areas of pain that are not sufficiently addressed by therapy. In various examples, patient feedback is also received after a therapy is changed. For example, the system may receive a confirmation or message from a patient indicating that a programming change produced a positive result, such as a reduction in pain. In various examples, patient feedback may also be sensed information such as heart rate, respiration rate, blood pressure, core or surface temperature, or other biologic information.

In various examples, a patient device is configured to receive inputs that are supplied remotely by a health care provider and delivered over a network to the patient device. The inputs are converted into programming instructions by the patient device. Programming rules may be applied to assure safety of the programming instructions. The rules may relate to a therapy delivered by the device, such as the amplitude of a stimulation therapy. For example, the rules may assure adherence to specified safety thresholds. Rules may also relate to the context under which the programming instructions are delivered to the device, such as when network connectivity between the patient device and a remote device is sufficiently strong, or when connectivity between the patient device and an implantable or wearable device is sufficiently strong (e.g. the device is in range of the patient device).

In various examples, the patient device includes or communicates with a patient feedback device. In various examples, the patient feedback device captures information that can be useful to a health care provider in assessing the patient or the effectiveness of therapy delivered according to new or previously-implemented programming settings. In various examples, the patient feedback device includes a camera to capture an image of the patient's face or some other portion of the patient, EKG data, surface temperature, internal (e.g. core) temperature, heart rate, respiration, speech, text, or other information.

In various examples, neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation. Deep Brain Stimulation (DBS) has been applied therapeutically for well over a decade for the treatment of neurological disorders, including Parkinson's Disease, essential tremor, dystonia, and epilepsy, to name but a few. Functional Electrical Stimulation (FES) has been used to restore or improve function of paralyzed muscles.

These implantable neurostimulation systems may include one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. A single stimulation lead may contain electrodes of different sizes. The neurostimulation system may further comprise an external therapy controller that can communicate with the neurostimulator to deliver instructions to generate electrical stimulation pulses in accordance with selected electrical stimulation parameters.

Electrical stimulation energy may be delivered from the neurostimulator to the electrodes in the form of an electrical pulsed waveform. Thus, the stimulation energy may be controllably delivered to the electrodes to stimulate the tissue. The set of electrodes, including those on and off the lead, used to deliver the electrical pulses to the targeted tissue constitutes an electrode set, with the electrodes capable of being selectively programmed to act as anodes (positive), cathodes (negative), and/or left off (zero). In other words, an electrode set represents the polarity being positive, negative, or zero. Other parameters that may be controlled or varied include, but are not limited to, the amplitude, width, rate, regularity, and ramp of the electrical pulses provided through the electrode array. Each electrode set, along with its electrical pulse parameters, can be referred to as a "stimulation parameter set."

With some neurostimulation systems, and in particular, those with independently controlled current and/or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e. fractionalized electrode sets).

An external therapy controller can be used to instruct the neurostimulator to generate electrical stimulation pulses in accordance with selected stimulation parameters. Typically, the stimulation parameters programmed into the neurostimulator can be adjusted by the user by manipulating controls on the external user therapy controller to modify the electrical stimulation provided by the neurostimulator system to the patient. Thus, in accordance with the stimulation parameters programmed by the external therapy controller, electrical pulses can be delivered from the neurostimulator to the stimulation electrode(s) to stimulate, activate, or affect a volume of tissue in accordance with the set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the amount of non-target tissue that is stimulated. A stimulation parameter set may include the electrodes that acting as anodes or cathodes, as well as the amplitude, duration, and rate of the stimulation pulses.

In various examples, to facilitate the selection of the stimulation parameters, the clinician uses a computerized programming system, which may include a networked therapy controller, to generate inputs that are converted into programming instructions. The programming system can be a self-contained hardware/software system, or can be defined predominately by software that is run on a standard personal computer (PC). The PC or custom hardware may actively control the characteristics of the electrical stimulation generated by the neurostimulator to allow the optimum stimulation parameters to be determined based on patient feedback, or other means, and to subsequently program the external therapy controller with the optimum electrical stimulation parameters. In various examples, the computerized programming system communicates over a network with a therapy controller in the vicinity of a patient.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external therapy controller, and if applicable the neurostimulator, with a set of stimulation parameters that best addresses the disorder or painful site.

Significantly, there are limits to how much charge (both in terms of total charge per pulse (or phase) and charge density per pulse) can be injected into tissue using one manner (e.g. biphasic, charge-balanced waveforms) without causing cell trauma and/or electrochemical damage (i.e., corrosion) to the electrodes. Each electrode, depending upon its physical properties (which include, but are not limited to, its size, shape, material, surface characteristics, and/or state), has a charge threshold level (which may also be affected by implant location, adjacent tissue type, and other biological factors) that should not be exceeded to ensure that the amount of charge applied to the electrode will not cause irreparable electrochemical harm to the electrode or induce cellular trauma. Smaller sized electrodes generally have lower charge threshold levels than larger sized electrodes that are manufactured of the same material because the smaller sized electrodes have higher charge densities.

Thus, with regard to tissue safety, both total charge and charge density have been taken into account to avoid cell trauma. As such, the Shannon model, which accounts for a single electrode of a surface area "A" through which a charge amount "Q" is injected, was created in 1992 for evaluating tissue safety limits. (See Shannon, R. V., A Model of Safe Levels for Electrical Stimulation, IEEE-TBME, Vol. 39, No. 4, pp. 424-426, April 1992).

Various examples described herein involve remote programming of diagnostic or therapy features in a spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves are also illustrated, including a dorsal root (DR) 105, dorsal root ganglion 106 and ventral root 107. The dorsal root 105 mostly carries sensory signals into the spinal cord, and the ventral root functions as an efferent motor root. The dorsal and ventral roots join to form mixed spinal nerves 108.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Some examples may deliver supra-perception SCS therapy, such as conventional SCS therapy that creates paresthesia. Although alternative or artifactual sensations, such as paresthesia, are usually tolerated relative to the sensation of pain, patients sometimes report these sensations to be uncomfortable. Some examples deliver sub-perception SCS therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some examples herein selectively modulate DH tissue or DR tissue over DC tissue to provide sub-perception therapy. Such selective modulation is not delivered at these higher frequencies. For example, the selective modulation may be delivered at frequencies at or less than 1,200 Hz. The selective modulation may be delivered at frequencies at or less than 1,000 Hz in some examples. In some examples, the selective modulation may be delivered at frequencies at or less than 500 Hz. In some examples, the selective modulation may be delivered at frequencies at or less than 350 Hz. In some examples, the selective modulation may be delivered at frequencies at or less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
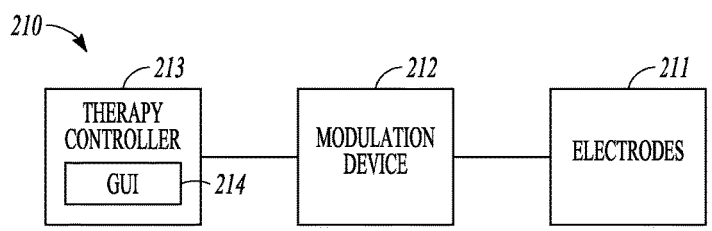
FIG. 2 illustrates, by way of example, an embodiment of a neuromodulation system.

FIG. 2 illustrates an embodiment of a neuromodulation system. The illustrated system 210 includes electrodes 211, a modulation device 212, and a therapy controller 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various examples, at least some parameters of the plurality of modulation parameters are programmable by a user, such as a physician or other caregiver. The therapy controller 213 provides the user with accessibility to the user-programmable parameters. In various examples, the therapy controller 213 is configured to be communicatively coupled to modulation device via a wired or wireless link. In various examples, the therapy controller 213 includes a graphical user interface (GUI) 214 that allows the user to set and/or adjust values of the user-programmable modulation parameters.

Figure 3:
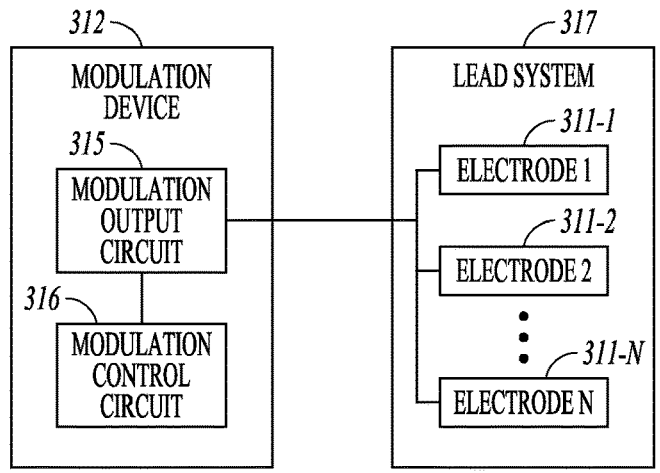
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads, where N≥2. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. In some examples, the lead system may include a paddle lead.

The neuromodulation system may be configured to therapeutically modulate spinal target tissue or other neural tissue. In various examples, the neuromodulation system may be configured to deliver one or more of Spinal Cord Stimulation (SCS), Deep Brain Stimulation (DBS), Peripheral Nerve Stimulation (PNS), and Functional Electrical Stimulation (FES). Some SCS examples are discussed below, but the present subject matter is not limited to SCS. The therapeutic modulation may be supra-perception modulation or sub-perception modulation. As will be described in more detail below, the neuromodulation system may be configured to deliver supra-perception modulation to dorsal roots for use in placing the electrode arrangement in position to deliver a therapy. In addition or as an alternative to delivering supra-perception modulation to dorsal roots for use in placing the electrode arrangement, the neuromodulation system may be configured to deliver supra-perception modulation to dorsal roots for use in programming the modulation field using a placed electrode arrangement. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Conventional programming for SCS therapy uses paresthesia to select an appropriate modulation parameter set. The paresthesia induced by the modulation and perceived by the patient should be located in approximately the same place in the patient's body as the pain that is the target of treatment.

When leads are implanted within the patient, an operating room (OR) mapping procedure may be performed to apply electrical modulation to test placement of the leads and/or electrodes, thereby assuring that the leads and/or electrodes are implanted in effective locations within the patient. Various examples use a modulation parameter set that includes supra-perception threshold dorsal root modulation field parameter data to intentionally modulate dorsal roots during the placement of the leads and/or electrodes. Various examples use a modulation parameter set that includes supra-perception threshold dorsal root modulation field parameter data to intentionally modulate dorsal roots after placement of the lead(s). For example, the supra-perception threshold dorsal root modulation field parameter data may be used to guide subsequent programming of the modulation field(s), or may be used to provide registration and mapping using the dorsal root location and lead location as a reference. One reason why there is so much intrapatient variability in terms of optimal SCS lead placement to treat any specific pain area (e.g. low back) may be that the bony anatomy and neuroanatomy are varied in their spatial relationship from patient to patient. Although neuroanatomy and bony anatomy are related, they can differ. An x-ray can show bony anatomy, but cannot show the spinal cord. Therefore, use of imaging techniques to use the bony anatomy alone to place the lead and/or electrodes may not accurately place the lead and/or electrodes. It may be desirable to think primarily about the neuroanatomy when programming a patient. The dorsal roots have a more predictable and reliable relationship to the spinal bony anatomy than the cord because the neuroforamina through which they travel is small and predictable in location. Dorsal roots are heterogeneous, as they include other fibers than that which is targeted. Therefore, dorsal root paresthesias are normally avoided in SCS since they have an increased likelihood of being uncomfortable.

However, various examples described herein use dorsal root paresthesias (or other patient-perceived sensation to the dorsal root modulation) for the purpose of determining the neurological position of the SCS lead(s). The position of the lead(s) is thus determined with respect to neuroanatomy and not just bony anatomy. Therefore, the root location need not be reliable with respect to bony anatomy. There is more predictability and consistency across patients as the foramina, through which the nerve roots travel, are in the same region. Specific programming parameters can be used to elicit and determine the location of the paresthesias that can be attributable to the dorsal roots. For example, some parameters may include low pulse width (e.g. less than 100 μs such as pulse widths within a range from 20 μs to 50 μs), monopolar modulation, anodal fields or cathodal fields. In a monopolar configuration, a case electrode on the IPG may be one of the cathode or anode, and electrode(s) on the lead may be the other one of the cathode or anode. The patient can identify where the dorsal paresthesias are felt to determine the location of the electrode arrangement. For example, the patient may identify the location of the paresthesia on a body image displayed on an external device.

Once the leads are correctly positioned, a fitting procedure, which may be referred to as a navigation session, may be performed to program the external therapy controller, and if applicable the neuromodulation device, with a set of modulation parameters that best addresses the painful site. Thus, the navigation session may be used to pinpoint the volume of activation (VOA) or areas correlating to the pain. The procedure may be implemented to target the tissue during implantation, or after implantation to target the tissue. The exact location is not necessarily determined during the operation. Rather, the device may be programmed to search for the desired modulation target or to refine the location of the desired modulation target. The procedure may be implemented if the leads gradually or unexpectedly move causing the modulation energy to move away from the target site. The supra-perception modulation of the dorsal roots may be part of this calibration and search process after implant or after suspected lead movement. By reprogramming the neuromodulation device (typically by independently varying the modulation energy on the electrodes), the VOA can often be moved back to the effective pain site without having to re-operate on the patient in order to reposition the lead and its electrode array. When adjusting the VOA relative to the tissue, it is desirable to make small changes in the proportions of current, so that changes in the spatial recruitment of nerve fibers will be perceived by the patient as being smooth and continuous and to have incremental targeting capability.

Figure 4:
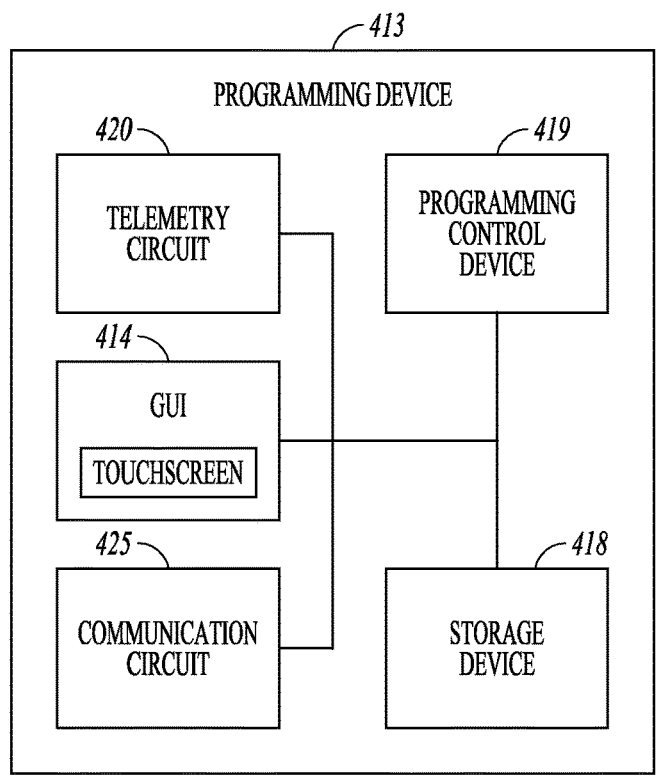
FIG. 4 illustrates, by way of example, an embodiment of a programming device, such as may be implemented as the programming device in the neuromodulation system of FIG. 2.

FIG. 4 illustrates an embodiment of a therapy controller 413, which may be implemented as the therapy controller 213 in the neuromodulation system of FIG. 2. The therapy controller includes a processor such as a programming control circuit 419, a telemetry circuit 420, and a communication circuit 425. The therapy controller 413 may also include a storage device 418, such as a memory circuit, and a user interface 414 such as a GUI, which may include a touchscreen.

The telemetry circuit 420 may for example be a MICS band telemetry circuit configured to communicate with a telemetry circuit in an implantable, wearable, or temporary medical device. The communication circuit 425 may for example be a local area wireless network (e.g. Wi-Fi) circuit, a cellular communication circuit, or any other kind of wired or wireless device. The GUI 414 may include any type of presentation device, such as interactive or non-interactive screens, and any type of user input devices that allow the user to program the modulation parameters, such as touchscreen, keyboard, keypad, touchpad, trackball, joystick, and mouse.

In an example, an input is received by the communication circuit 425 or user interface circuit 414 and delivered to the programming control circuit 419, which converts the input into programming instructions and checks the programming instructions against a set of rules. When the programming instructions comply with the rules, the therapy controller 413 delivers the programming instructions to a medical device using the telemetry circuit 419. In an example, the rules verify the safety of the proposed programming instructions, for example by assuring that specified safety limits (e.g. neurostimulation energy density limits) are not exceeded. Other rules may also depend on the environment of the implantable or wearable device or connectivity of the therapy controller to the device or to a remote device. In some examples, programming is applied only when communication connectivity between the implanted device and therapy controlled meets specified criteria (e.g. absence of excessive noise or presence of specified signal strength), or when communication connectivity between the therapy controller and the remote device (e.g. network connectivity) meets specified criteria. In various examples, the therapy controller 413 sends information about the operation of the device, e.g. to report a successful programming change, through the communication circuit 425 for delivery to a remote device.

In various examples that involve neuromodulation therapy, the programming control circuit 419 generates a plurality of modulation parameters that control the delivery of the neuromodulation pulses according to the pattern of the neuromodulation pulses. For example, the programming control circuit 419 may generate the plurality of modulation parameters using inputs received from the GUI, from a remote device over a network, or a combination thereof. In various examples, the programming control circuit 419 may check values of the plurality of modulation parameters against safety rules to limit these values within constraints of the safety rules.

The storage device 418 may store, among other things, modulation parameters to be programmed into the modulation device. The modulation parameters may be organized into one or more sets of modulation parameters. Thus, some examples may provide supra-perception threshold dorsal root modulation field parameter data in a set of modulation parameters and may provide therapeutic modulation field parameter data in another set of modulation parameters. In response to a command from the programming control circuit, the stored parameters may be retrieved from the memory device and delivered to an implantable or wearable device.

In various examples, the therapy controller 413 transmits the plurality of modulation parameters to the modulation device 312 using the telemetry circuit 420 when one or more rules are satisfied, such as safety limit rules, network connectivity rules, and medical device connectivity rules. In some examples, the therapy controller 413 may also transmit power to the modulation device.

In various examples, the therapy controller 413, including its various examples discussed in this document, may be implemented using a combination of hardware, software and firmware. For example, the circuit of GUI, modulation control circuit, and programming control circuit, including their various examples discussed in this document, may be implemented using an application-specific circuit constructed to perform one or more particular functions, or a general-purpose circuit programmed to perform such function(s). Such a general-purpose circuit includes, but is not limited to, a microprocessor or a portion thereof, a microcontroller or portions thereof, and a programmable logic circuit or a portion thereof. Thus, while the therapy controller is may be implemented as a piece of specialized hardware, the therapy controller may also be implemented as a standard personal computer (PC), or standard personal electronic device such as a mobile phone or tablet, that is running specialized software or has specialized attachments (e.g. a Bluetooth or US-B wand for communication, or sensors).

Figure 5:
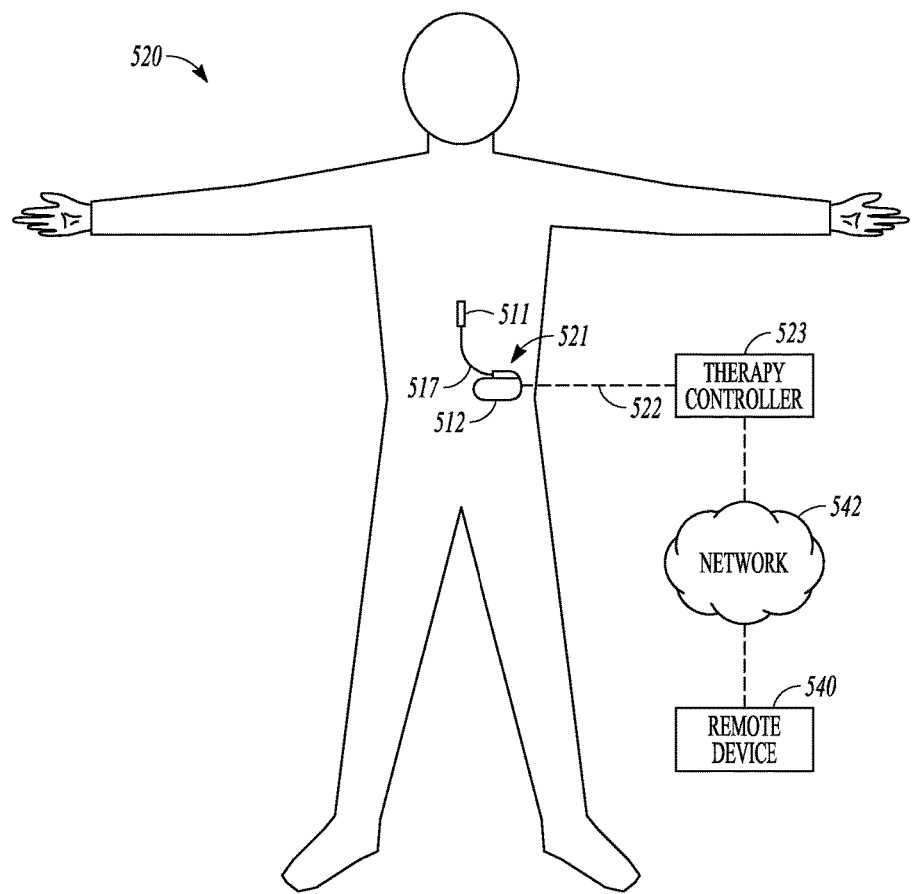
FIG. 5 illustrates, by way of example, an implantable neuromodulation system and portions of an environment in which system may be used.

FIG. 5 illustrates, by way of example, a remote medical device programming system 520 including an implantable or wearable system 521, a local external system 522, and a telemetry link 523 providing for wireless communication between implantable system 521 and external system 522. The system 520 may also include a remote device 540 that can communicate with the local external system 522 over a network 542 such as a local area network (LAN), wireless network, the internet, or a combination thereof. In an example, the medical device system is an implantable or wearable system, such as a neuromodulation system or cardiac rhythm management system. The medical device may also be a non-implanted trial device. The device may be operatively coupled to permanently implanted or temporarily implanted leads, or surface lead.

The system may also include a patient feedback device 550, which may be a stand-alone device, or integrated into the therapy controller. In an example, the patient feedback device includes a camera that captures a still image, series of images, or video of a portion of a patient, such as the patient's face (e.g. to detect a wince or response to pain.) In various examples, the patient feedback device may include a microphone, touchscreen, keyboard, fingerprint sensor, EKG system, thermometer, posture sensor, or pressure sensor.

In an example, the remote device 540 includes a user interface circuit configured to receive an input relating to the operation implantable or wearable medical device, and a remote device communication circuit configured communicate with a network apparatus to deliver the input over a network to the therapy controller 523. In some examples, the system 520 also includes circuits to support communication with the patient, such as a camera or microphone on the remote device 540 or otherwise operatively coupled with the network to enable communication with the patient.

For the purpose of illustration, the system is shown positioned near the spinal cord, but it may be implanted elsewhere, which leads extending to target locations to effectuate the various therapies discussed herein. In an example, the implantable system 521 includes an implantable device (also referred to as an implantable pulse generator, or IPG) 512, a lead system 517, and electrodes 511. The lead system 517 includes one or more leads each configured to be electrically connected to the implantable device 512, and a plurality of electrodes 511 distributed in the one or more leads. In various examples, the external system 402 includes one or more external (non-implantable) devices each allowing a user (e.g. a clinician or other caregiver and/or the patient) to communicate with the implantable system 521.

The external system 522 includes a therapy controller 523. The therapy controller 523 may, for example, be a programming device intended for a clinician or other caregiver to initialize and adjust settings for the implantable system 521. In another example, the therapy controller is a patient therapy controller intended for use by the patient. The patient therapy controller may provide the patient with a limited set of therapy controls, such as controls that allow the patient to turn a therapy on and off, or to adjust certain patient-programmable parameters of the plurality of modulation parameters.

In an example, the neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
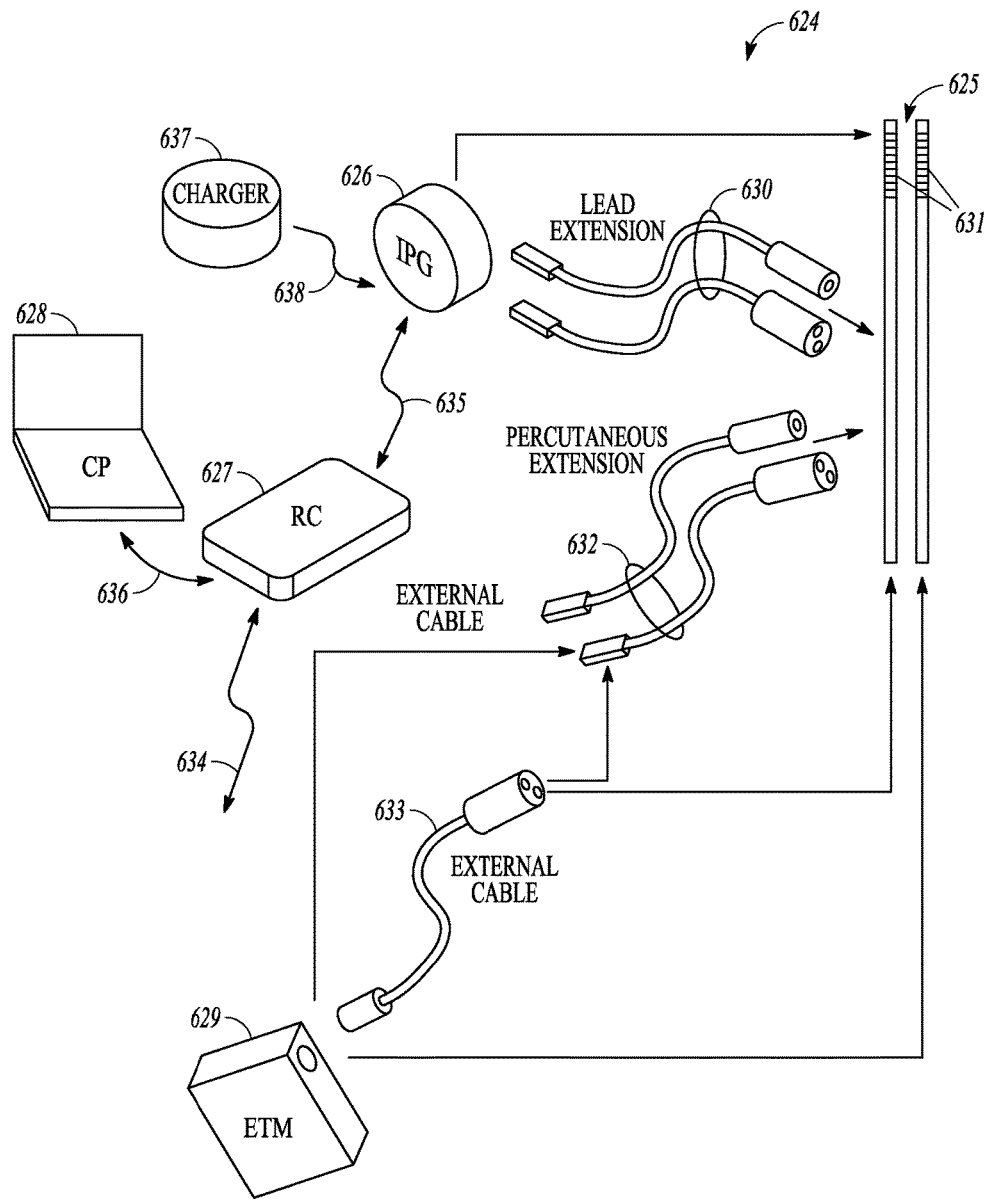
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an implantable pulse generator (IPG) 626, an external therapy controller therapy controller 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. The electrodes, when implanted in a patient, form an electrode arrangement. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical modulation energy to the electrodes accordance with a set of modulation parameters. The ETM 629 is a non-implantable device that may be used on a trial basis after the neuromodulation leads 625 have been implanted and prior to implantation of the IPG 626, to test the responsiveness of the modulation that is to be provided. Functions described herein with respect to the IPG 626 can likewise be performed with respect to the ETM 629.

The therapy controller 627 (TC) may be used to telemetrically control the ETM 629 via a bi-directional RF communications link 634. The therapy controller 627 may be used to telemetrically control the IPG 626 via a bi-directional RF communications link 635. Such control allows the IPG 626 to be turned on or off and to be programmed with different modulation parameter sets. The IPG 626 may also be operated to modify the programmed modulation parameters to actively control the characteristics of the electrical modulation energy output by the IPG 626. A clinician may use the CP 628 to program modulation parameters into the IPG 626 and ETM 629 in the operating room and in follow-up sessions.

Figure 9:
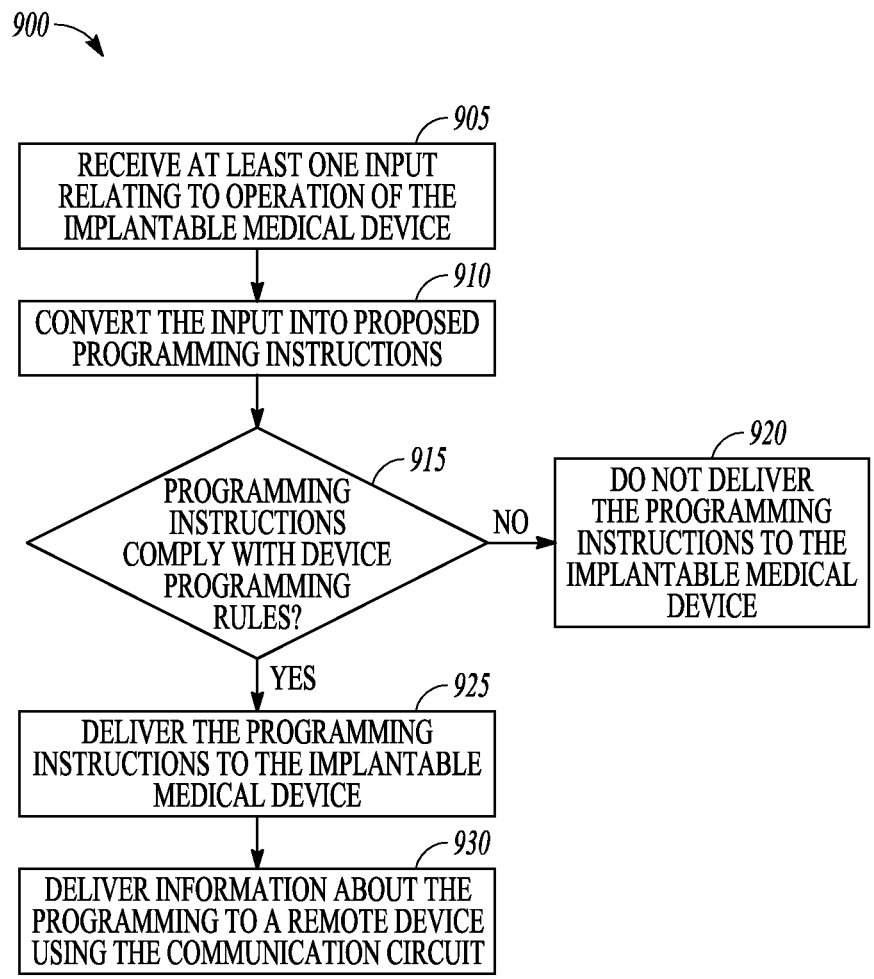
FIG. 9 is a flowchart that illustrates an example method of remotely controlling the operation of an implantable or wearable medical device using a remote medical device programming system.
Figure 10:
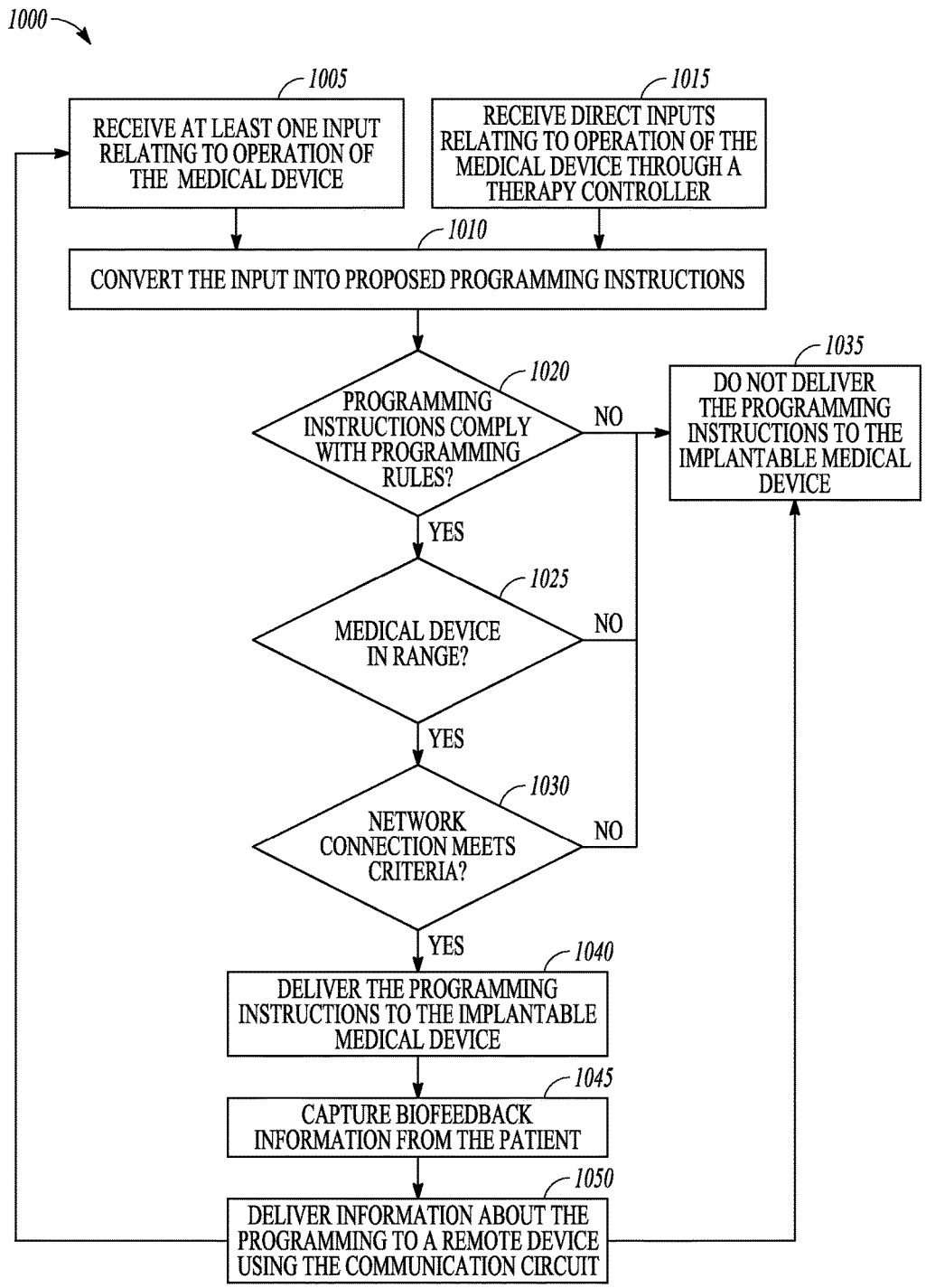
FIG. 10 is a flowchart that illustrates another example method of remotely controlling the operation of an implantable or wearable medical device using a remote medical device programming system.

The CP 628 may indirectly communicate with the IPG 626 or ETM 629, through the therapy controller 627, via an IR communications link 636 or other link. The CP 628 may directly communicate with the IPG 626 or ETM 629 via an RF communications link or other link (not shown). The clinician detailed modulation parameters provided by the CP 628 may also be used to program the therapy controller 627, so that the modulation parameters can be subsequently modified by operation of the therapy controller 627 in a stand-alone mode (i.e., without the assistance of the CP 628). In some examples, the CP 628 may receive inputs that are transferred over a network, such as the internet, to a therapy controller that tis in the vicinity of a patient. Example methods remote programming using such a system is illustrated in FIGS. 9 and 10. Various devices may function as the CP 628. Such devices may include portable devices such as a lap-top personal computer, mini-computer, tablet, phone, or specialized hardware. Thus, the programming methodologies can be performed by executing software instructions contained within the CP 628. Alternatively, such programming methodologies can be performed using firmware or hardware. In any event, the CP 628 may actively control the characteristics of the electrical modulation generated by the IPG 626 to allow the desired parameters to be determined based on patient feedback or other feedback and for subsequently programming the IPG 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting. The external device(s) (e.g. CP and/or TC) may be configured to communicate with other device(s), including local device(s) and/or remote device(s). For example, wired and/or wireless communication may be used to communicate between or among the devices.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the TC or CP being present.

Figure 7:
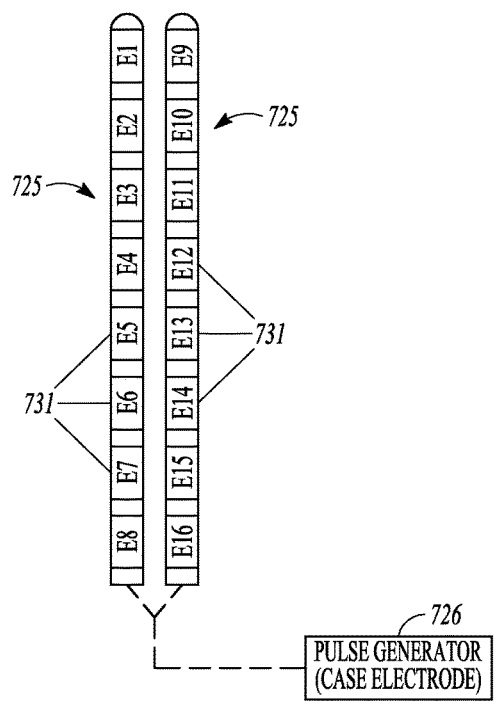
FIG. 7 illustrates, by way of example, some features of the neuromodulation leads and a pulse generator.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG. Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (which may be measured in milliamps or volts depending on whether the pulse generator supplies constant current or constant voltage to the electrode array), pulse width (which may be measured in microseconds), pulse rate (which may be measured in pulses per second), and burst rate (which may be measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The IPG may be configured to individually control the magnitude of electrical current flowing through each of the electrodes. For example, a current generator may be configured to selectively generate individual current-regulated amplitudes from independent current sources for each electrode. In some examples, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

As identified earlier, when leads are implanted within the patient, an operating room (OR) mapping procedure may be performed to apply electrical modulation to test placement of the leads and/or electrodes, thereby assuring that the leads and/or electrodes are implanted in effective locations within the patient. Various examples use a modulation parameter set that includes supra-perception threshold dorsal root modulation field parameter data to intentionally modulate dorsal roots during the placement of the leads and/or electrodes. One reason why there is so much intrapatient variability in terms of optimal SCS lead placement to treat any specific pain area (e.g. low back) may be that the bony anatomy and neuroanatomy are varied in their spatial relationship from patient to patient.

Figure 8:
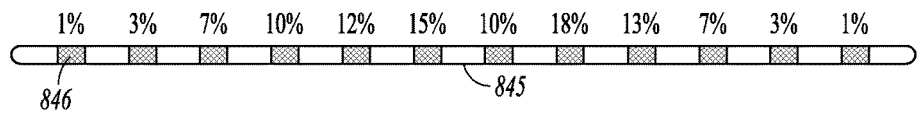
FIG. 8 is a schematic view of the electrical modulation lead showing an example of the fractionalization of the anodic current delivered to the electrodes on the electrical modulation lead.

FIG. 8 is a schematic view of the electrical modulation lead 845 showing an example of the fractionalization of the anodic current delivered to the electrodes on the electrical modulation lead. These figures illustrate fractionalization using monopolar modulation where a case electrode of the IPG is the only cathode, and carries 100% of the cathodic current. The fractionalization of the anodic current shown in FIG. 8 does not deliver an equal amount of current to each electrode 846, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 8, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various examples may implement a programmed algorithm to determine the appropriate fractionalization to achieve a desired modulation field property (e.g. constant electric field, or constant electric field magnitude, or constant voltage).

Therefore, as illustrated by the above examples, there may be a very large number of possible programming settings. Some of these settings may not be desirable. Various examples may implement device programming rules to verify the safety of the proposed programming instructions.

Referring now to FIG. 9, an example method 900 of remotely programming an implantable or wearable medical includes receiving at 905 at least one input relating to operation of an implantable or wearable medical device. In various examples, the implantable or wearable medical device includes a Spinal Cord Stimulation (SCS), Deep Brain Stimulation (DBS), Peripheral Nerve Stimulation (PNS), and Functional Electrical Stimulation (FES), or trial stimulator.

In various examples, the receiving 905 includes receiving information from a remote device that accepted the inputs and transferred them over a network. In reference to the example system shown FIG. 5, a user may provide the input to the remote device 540 which delivers it over a network 542 such as the interne to the therapy controller 523, which receives and processes the input. In various examples, the input transferred by a remoted device 540 is received by therapy controller 213, 413, 523, for example using communication circuit 425 or user interface circuit 414. The data transmitted between remote device and the therapy controller is a secure transmission. For example an encrypted protocol may be used for to encrypt patient identifying information, programming parameters, or physiologic data. In an example, a public key cryptography system is used to secure data. In an example, the received inputs are stored in a memory circuit and retrieved for processing by a processor.

At 910, the at least one input is converted into proposed programming instructions. The programming instructions may include, for example, specific parameter settings to be set in the device to alter operation of the device in accordance with the input. In some examples, the programming instructions include instructions to download a previously-verified program from a remote device, and install the program on the therapy controller. The clinician may create "programs" for the patient which contains the parameter setting for their therapies, which are stored in a memory circuit or other storage device on a therapy controller, and used by the patient to control the device, e.g. to control therapy. The patient has limited control over the therapy, for example increasing the strength of the therapy, subject to certain rules. In an example, the programs are stored remotely on a remote memory circuit, so that if the therapy controller loses the program (e.g. it is deleted or corrupted), the therapy controller may access the remote device, which stored the program settings during or after the program session, and restore the program settings in the memory circuit therapy controller.

At 915, the method applies device programming rules to verify the safety of the proposed programming instructions. For example, with spinal cord stimulation therapy, the therapy should not exceed certain rates and charge densities to avoid damaging tissue. For example, if a certain pulse width and rate have been prescribed, the therapy should not exceed a specified amplitude to avoid creating charge densities that exceed safety limits. In an example, the rules match validated rules applied to a clinician programmer. In an example, a processor such as the therapy control device 419 shown in FIG. 4 applies the device programming rules.

At 920, if the programming instructions do not comply with device programming rules, the therapy controller 523 does not deliver the programming instructions to the implantable or wearable medical device.

When the programming instructions comply with the device programming rules, at 925 the therapy controller delivers the programming instructions to the implantable or wearable medical device. In some examples, the therapy controller first checks the quality of a network connection to the remote device before delivering the instructions to assure that connectivity between the remote device and the implantable or wearable remains in place during and after the transmission of programming instructions. This may allow, for example, corrective action if the programming instructions turn out to be incompatible with or undesirable for the patient.

At 930, the therapy controller delivers information about the programming to a remote device using a communication circuit. In various examples, the therapy controller delivers a confirmation that the programming was successful, or information about the patient, device, or therapy.

In an example, the system accommodates programming inputs both locally and remotely. In an example, the therapy controller applies programming rules in the same manner regardless of whether the input originated from the therapy controller or the remote device. This can be advantageous, because the same set of clinically-validated safety and efficacy rules can be applied across programming platforms, reducing cost and training burden. In various examples, user interface automation is used to convert inputs relating to the operation of the implantable or wearable device into proposed programming instructions. In an example, this allows a physician to select particular therapy or diagnostic features or outcomes, while the therapy controller uses the input to convert those selections into program setting for the implanted device.

In some examples, delivering information 930 to a remote device includes feedback from the patient. In various examples, feedback delivered from the patient to the remote device includes video (e.g. visual indication of pain or relief), audio (e.g. verbal report or physiologic response), text (e.g. keyboard input), or sensed physiologic information (e.g. temperature, blood pressure, respiration rate, pulse rate, heart sound, or EKG data.) For example, a patient may communicate that she felt stimulation in the wrong leg, or that they are feeling relief in the correct therapy target (e.g. an injured leg.) In some examples, the patient feedback device also includes a display configured to present to the patient at least one image of a person who is remotely providing the at least one input relating to operation of the implantable medical device. This can provide confidence that the programming inputs are from the patient's physician, or another authorized health care professional.

Referring now to FIG. 10, a method 1000 of controlling the operation of an implantable or wearable medical device using a remote medical device programming system includes at 1005 receiving at least one input relating to operation of the medical device and at 1010 converting the input into proposed programming instructions. In an example, the inputs are received by a therapy controller over a network from a remote device that is used by a health care professional such as a physician. The method 1000 may also include at 1015 receiving direct inputs relating to the operation of the medical device through the therapy controller. In various examples, inputs are converted into proposed programming instructions in the same manner and are subject to the set of device programming rules executed by the therapy controller, regardless of whether the inputs are received 1005 from the remote device or directly 1015 through the therapy controller.

In some examples, a device such as a therapy controller executes user interface automation instructions to convert the received inputs into programming instructions, or to apply rules (as described below.) While the method is applicable for implantable and wearable devices, such as implantable or trial wearable neurostimulation devices, for simplicity and readability, FIG. 10 references only implantable devices, but it is understood that the example is also applicable to wearable devices.

Referring again to FIG. 10, at 1020, 1025, 1030, programming rules are applied. In various examples, only one or two of the rules 1020, 1025, 1030 are applied, or they are applied in different order. At 1020, device programming rules are applied. For example, the rules enforce therapy safety limits as discussed above. If the programming rules are not satisfied, at 1030, the programming instructions are not delivered, or not installed, on the implantable or wearable device. At 1025, if the medical device is not sufficiently in range of the therapy controller, e.g. the connection between the therapy controller and the medical device does not meet specified criteria, the programming instructions are not delivered. At 1030, if the network connection between the therapy controller and the remote device does not meet specified criteria, the programming instructions are not delivered. Consistent network connectivity can be desirable during programming so that patient or device condition or operation can be monitored and after remote programming. When the programming instructions comply with programming rules, the device is in range, and the network connection between the therapy controller meets specified criteria, at 1040 the programming instructions are delivered to the medical device. At 1045, the biofeedback information may be captured from the patient after the new programming instructions are delivered and installed on the medical device. The biofeedback information may be subjective information supplied by the patient, for example through text (e.g. keyboard or voice recognition), audio, video, or responses to survey questions. The biofeedback may also be observational, e.g. a still image or video image of the patient's face or some or all of the patient's body, or sensed data, such as pulse rate, respiration rate, blood pressure, core or surface temperature, posture, activity or movement. At 1050, information about the programming is delivered to the remote device. In some examples, a second input is received, for example based on the biofeedback information, and converted into programming instructions.

In some examples, a programming protocol involves progressively increasing or decreasing a magnitude of a stimulation therapy, and stopping the progressive increase in magnitude when a network connection with a remote device does not meet specified criteria, or other rules are violated.

In an example, the programming instructions include a previously-verified program delivered from a remote device, and installed the program on the therapy controller to control operation of the implantable or wearable device.

In an example, a therapy controller in proximity to the patient, which may be therapy controller 413 shown in FIG. 4 or therapy controller 523 shown in FIG. 5 receives 1005, 1010 the input from a network such as network 542 or through a user interface 414, a programming control circuit 419 converts the input into programming instructions 1010, which may include retrieving programming information from a storage device 418, and the programming control circuit 419 applies one or more rule sets 1020, 1025, 1030, and delivers the programming instructions to the implantable or wearable device, or a trial device, for example using a telemetry circuit such as telemetry circuit 420. In various examples, the therapy controller 413 gathers biofeedback information 1045 using an integrated sensor in the therapy controller, or by communication with one or more additional devices (not shown) that collect biofeedback information through user interface or sensors or both.

The above detailed description is intended to be illustrative, and not restrictive. The scope of the disclosure should, therefore, be determined with references to the appended claims, along with the full scope of equivalents to which such claims are entitled

What is claimed is:

1. A system comprising:
    a therapy controller including a telemetry circuit configured to communicate with an implantable or wearable medical device and a processor configured to execute instructions relating to programming the implantable or wearable medical device; and
    a communication circuit operatively coupled to the therapy controller and configured to transfer information between the therapy controller and a remote device;
    the therapy controller configured to:
    receive at least one input relating to operation of the implantable or wearable medical device;
    convert the at least one input into proposed programming instructions;
    apply device programming rules to verify the safety of the proposed programming instructions;
    deliver the programming instructions to the implantable or wearable medical device when the programming instructions comply with the rules;
    deliver information about the programming to a remote device using the communication circuit;
    wherein the therapy controller is configured to ramp up or down the strength of a stimulation therapy, monitor the quality a network connection to a remote device, and stop the ramp up or down in response to a determination that the network connection does not meet one or more specified criterion.

2. The system of claim 1, further comprising a patient feedback device configured to receive feedback information from a patient, wherein the therapy controller is configured to deliver the feedback information from the patient to the remote device using the communication circuit.

3. The system of claim 2, wherein the patient feedback device comprises a camera and the feedback information comprises at least one image of a facial expression or body position or movement of a patient.

4. The system of claim 2, wherein the patient feedback device is configured to capture one or more of a verbal report, a visual indication, a keyboard input, and sensed physiologic information from the patient.

5. The system of claim 2, wherein the patient feedback device includes a display configured to present to the patient at least one image of a person who is remotely providing the at least one input relating to operation of the implantable or wearable medical device.

6. The system of claim 1, further comprising the implantable or wearable medical device.

7. The system of claim 1, wherein the therapy controller further comprises a user interface circuit configured to receive the at least one input relating to operation of the implantable or wearable medical device, and the controller is configured to convert the at least one input into programming instructions and apply device programming rules in the same manner regardless of whether the at least one input originated from the therapy controller or the remote device.

8. The system of claim 7, wherein the therapy controller includes a circuit configured to execute user-interface automation instructions to convert the at least one input relating to operation of the implantable or wearable medical device into the proposed programming instructions.

9. The system of claim 1, wherein the therapy controller is further configured to receive an instruction to download a previously-verified program from a remote device, and install the program on the therapy controller.

10. The system of claim 1, wherein the therapy controller is a patient therapy controller.

11. The system of claim 1, wherein the therapy controller is configured to stop the ramp up or down in response to a determination that the network connection does not meet a plurality of specified criteria.

12. A remote medical device programming system comprising:
    a medical device including a patient circuit configured to interact with a body of a patient and a telemetry circuit configured to communicate with another device; and
    a therapy controller including a telemetry circuit configured to communicate with the medical device, a communication circuit configured to receive inputs from a remote device over a network, a user interface circuit configured to receive inputs relating to operation of the implantable or wearable medical device, and a processor configured to execute instructions relating to programming the implantable or wearable medical device;
    the therapy controller configured to:
    convert the received inputs into proposed programming instructions;
    apply device programming rules to verify the safety of the proposed programming instructions;
    deliver the programming instructions to an implantable or wearable medical device when the programming instructions comply with the rules,
    convert the inputs into proposed programming instructions and apply device programming rules in the same manner when the inputs are received through the therapy controller user interface and when then inputs are received from the remote device;
    wherein the therapy controller in configured to ramp up or down the strength of a stimulation therapy, monitor the quality a network connection to a remote device, and stop the ramp up or down in response to a determination that the network connection does not meet one or more specified criterion.

13. The remote medical device programming system of claim 12, further comprising the remote device, the remote device including a user interface circuit configured to receive the at least one input relating to operation of the medical device, and a communication circuit configured to transfer information to a network for delivery to the therapy controller.

14. The remote medical device programming system of claim 12, wherein the therapy controller is configured to execute user interface automation instructions to convert the at least one input and apply device programming rules.

15. The remote medical device programming system of claim 12, wherein the medical device includes an implantable neurostimulator.

16. A method of controlling the operation of an implantable or wearable medical device:
receiving through a communication circuit on a therapy controller at least one input from a remote device that relates to operation of the implantable or wearable medical device;
converting the at least one input into programming instructions;
applying device programming rules to verify the safety of the programming instructions;
delivering the programming instructions to the implantable or wearable medical device when the programming instructions comply with the rules and the implantable or wearable medical device is in range of a telemetry circuit on the therapy controller; and
progressively increasing or reducing a magnitude of a stimulation therapy, and stopping the progressive increase or decrease in magnitude when a network connection with a remote device does not meet a specified criterion.

17. The method of claim 16 further comprising capturing biofeedback information from the patient to assess whether the operation of the medical device is effective and sending the bio-feedback information to the remote device.

18. The method of claim 17, wherein capturing biofeedback information comprises capturing at least one image of a facial expression on the patient.

19. The method of claim 16, further comprising receiving direct inputs relating to operation of the implantable or wearable medical device directly through the therapy controller and converting the direct inputs into direct programming instructions, wherein inputs are converted into proposed programming instructions in the same manner and are subject to the set of device programming rules executed by the therapy controller, regardless of whether the inputs are received from the remote device or directly through the therapy controller.

20. The method of claim 16, further comprising monitoring the quality of a network connection to a remote device and refraining from implementing programming changes when the network connection does not meet specified criteria.

* * * * *